United States Patent [19]

Hillen et al.

[11] Patent Number: 4,736,020

[45] Date of Patent: Apr. 5, 1988

[54] PURIFICATION OF HTNF

[75] Inventors: Heinz Hillen; Peter Moesta; Stefan Marcinowski, all of Ludwigshafen, Fed. Rep. of Germany

[73] Assignee: BASF Aktiengesellschaft, Ludwigshafen, Fed. Rep. of Germany

[21] Appl. No.: 886,621

[22] Filed: Jul. 18, 1986

[30] Foreign Application Priority Data

Jul. 22, 1985 [DE] Fed. Rep. of Germany ....... 3526096

[51] Int. Cl.$^4$ .............................................. C07K 3/22
[52] U.S. Cl. .................................. 530/416; 530/412; 530/417; 530/351; 435/803; 435/68
[58] Field of Search ............... 530/416, 412, 417, 351; 435/803

[56] References Cited

FOREIGN PATENT DOCUMENTS

85/05631 12/1985 PCT Int'l Appl. .................. 435/68

OTHER PUBLICATIONS

Yamada et al, *CA*, vol. 104, #2050322, 1986.
Fiers et al, *WPI*, abstract to WO86/03751.
Richay, *Am. Laboratory*, 1982.
Fagenstrom et al, *J. Chromato*, 206, 1983, pp. 523–532.
Practical Protein Chemistry, 1986, ed. Darbre.
Mariya et al, *CA*, vol. 105, #207347a, 1986.
Kato et al, *CA*, vol. 105, #222217b, 1986.
Kato et al, Biochem. Biophys. Res. Comm., 1985, 130, pp. 692–699.
Proc. Nat. Acad. Sci. USA, vol. 72, No. 9, p. 3666 (1975).
Nature, vol. 312, 20/27 Dec. 1984.
Biological Chemistry, 260, 2345 (1985).

*Primary Examiner*—John Kight
*Assistant Examiner*—Garnette D. Draper
*Attorney, Agent, or Firm*—Keil & Weinkauf

[57] ABSTRACT

The purification of hTNF by ion exchange chromatography is described.

2 Claims, No Drawings

PURIFICATION OF hTNF

The present invention relates to a process for the purification of human Tumor Necrosis Factor (hTNF).

TNF was first described in 1975 [Proc. Nat. Acad. Sci. USA 72 (1975), 3666] as a factor which necrotizes the tumors produced in mice by induction with Calmette-Guerin bacillus. Cloning and expression of hTNF were carried out successfully in 1984 [Nature 312 (1984) 724]. Very soon afterward, the purification, production and characterization of the natural protein from a macrophage cell line (HL60) stimulated with phorbol ester was also reported [Biol. Chem. 260 (1985), 2345].

The expression of hTNF in recombinant E. coli strains leads as a rule to a mixture of hTNF and N-terminal methionine-containing hTNF. The expression of hTNF in E. coli is described in, for example, Nature 312 (1984) 724. The hTNF obtainable by this method and similar methods contains as a rule from 5 to 90% of N-terminal methionine, depending on the fermentation conditions. It should be noted that the active hTNF consists of three chains, one or more of which may carry methionine radicals on the ends. The hTNF obtained by expression of hTNF in E. coli therefore also contains hTNF carrying one, two or three methionine radicals.

We have found a process which makes it possible to obtain hTNF which is virtually free of methionine-hTNF.

The present invention relates to a process for the isolation of hTNF from a mixture of hTNF and N-terminal methionine-containing hTNF, wherein the said mixture is subjected to cation exchange chromatography over a cation exchanger containing sulfoaryl or sulfoalkyl groups.

Examples of suitable cation exchangers are those containing a sulfo-$C_1$–$C_4$-alkylene group, preferably the —$CH_2$–$SO_3^-$ group. Exchangers of this type are, in particular, MonoBeads, Mono S and S Sepharose ® Fast Flow, which are obtainable from Pharmacia, S-75 182 Uppsala.

MonoBeads, Mono S is a strong cation exchanger containing —$CH_2SO_3^\ominus$ groups. Its particle size is 9.8 $\mu m \pm 2\%$, its exclusion limit is $10^7$ daltons and it can be used in a pH range of from 2 to 12. It is preferably employed in prepacked FPLC columns (cf. prospectus entitled FPLC Separation Power from Deutsche Pharmacia GmbH, D-7800 Freiburg. S Sepharose ® Fast Flow is an exchanger based on crosslinked agarose (6%), with —$CH_2$—$SO_3^\beta$ counter-ions (cf. prospectus entitled R and S Sepharose ® Fast Flow from Pharmacia.

S Sepharose ® Fast Flow is a strong cation exchanger having a capacity of from 0.18 to 0.25 meq/ml of gel and an exclusion limit of $4 \times 10^6$ daltons. It can be used in a pH range of from 2 to 14 (cf. Product information bulletin entitled R and S Sepharose ® Fast Flow from Pharmacia.

The mixture of hTNF and methionine-containing hTNF (mixture to be separated) is introduced onto the column in a buffer at pH 2.0–9.5, preferably about 6.5–8.0. Elution can be effected using a pH gradient or salt gradient or a combination of the two. Before the mixture is applied, the column is equilibrated with a buffer. After application of the mixture, the pH and/or the salt concentration in the eluent is increased stepwise or, preferably, continuously until the desired fraction emerges from the column.

The solutions usually employed in chromatography can be used as the buffer, a phosphate buffer having proven most useful. The buffer concentration may be varied within wide limits (about 0.005–0.5 molar).

Preferred salts for gradient elution are the chlorides of alkali metals and alkaline earth metals, and ammonium chloride. Sodium chloride is particularly suitable.

The novel process permits the preparation of hTNF in a purity of not less than 99%. It thus meets the requirements set for pharmaceutical active compounds based on proteins.

It is surprising that two polypeptides which differ only in that one contains a neutral amino acid radical (methionine) can be separated by chromatography over a cation exchanger. Usually, only substances having substantially different charges can be separated by this method.

The Examples which follow illustrate the invention.

EXAMPLE 1

A MonoBeads, Mono S column (HR 16/10, Pharmacia) was equilibrated with 100 ml of 20 mM phosphate buffer at pH 7.7. 60 mg of crude hTNF in 2 ml of 20 mM phosphate buffer were introduced onto the column. A linear gradient was then applied using 120 ml of 20 mM phosphate buffer (pH 7.7) and 120 ml of 20 mM phosphate buffer (pH 7.7) which was 0.24M in sodium chloride. Peaks were obtained at 0.10M, 0.12M and 0.14M. The peak at 0.14M contained hTNF in a purity of 99%. By rechromatography under the same conditions, it was possible to increase the purity to 99.9%.

EXAMPLE 2

The process was carried out as described in Example 1, except that S Sepharose was used instead of MonoBeads, Mono S.

EXAMPLE 3

A column (1.1×20 cm) was packed with S Sepharose ® Fast Flow (Pharmacia) and equilibrated with 100 ml of 20 mM phosphate buffer at pH 7.0. 150 mg of crude hTNF were dissolved in 5 ml of 20 mM phosphate buffer (pH 7.0), and the solution was slowly (1 ml/min) introduced onto the column. The column was then washed with 30 ml of 20 mM phosphate buffer (pH 7.0), after which a linear gradient was applied using 250 ml of 20 mM phosphate buffer (pH 7.0) and 250 ml of 50 mM phosphate buffer (pH 9.0). Peaks were obtained at pH 7.95, 8.15 and 8.5. The peak at pH 8.5 contained hTNF in a purity of 98%. By rechromatography under the same conditions, it was possible to increase the purity to above 99%.

EXAMPLE 4

The process was carried out similarly to Example 3, except that Monobeads, Mono S was used instead of S Sepharose.

EXAMPLE 5

A column (1.1×20 cm) was packed with S Sepharos ® Fast Flow (Pharmacia) and equilibrated with 100 ml of 44 mM phosphate buffer at pH 8.34. 150 mg of crude hTNF were dissolved in 5 ml of 44 mM phosphate buffer at pH 8.34, and the solution was slowly (1 ml/min) introduced onto the column. Elution was then carried out with 30 ml of 44 mM phosphate buffer (pH 8.34) until the UV absorption at 280 nm had flattened out. The methionine-free TNF was then eluted with 50 mM phosphate buffer at pH 8.6 and was obtained in a purity of 98%. By rechromatography under the same conditions, it was possible to increase the purity to above 99%.

We claim:

1. A process for isolating hTNF from a mixture of hTNF and N-terminal methionine-containing hTNF comprising subjecting said mixture to cation exchange chromatography over a cation exchanger containing sulfoaryl or sulfoalkyl groups.

2. The process of claim 1 wherein the purity of the isolated hTNF is at least 99%.

* * * * *